US00PP15082P3

(12) United States Plant Patent
Zary

(10) Patent No.: US PP15,082 P2
(45) Date of Patent: Aug. 17, 2004

(54) SPRAY ROSE PLANT NAMED 'JACREWHI'

(50) Latin Name: *Rosa hybrida*
Varietal Denomination: JACrewhi

(75) Inventor: Keith W. Zary, Somis, CA (US)

(73) Assignee: Jackson & Perkins Wholesale, Inc., Somis, CA (US)

( * ) Notice: Subject to any disclaimer, the term of this patent is extended or adjusted under 35 U.S.C. 154(b) by 0 days.

(21) Appl. No.: 10/121,670

(22) Filed: Apr. 15, 2002

(65) Prior Publication Data

US 2003/0196233 P1 Oct. 16, 2003

(51) Int. Cl.[7] ..... A01H 5/00

(52) U.S. Cl. ..... Plt./143

(58) Field of Search ..... Plt./143

*Primary Examiner*—Anne Marie Grunberg
*Assistant Examiner*—Annette H Para
(74) *Attorney, Agent, or Firm*—Burns, Doane, Swecker & Mathis, L.L.P.

(57) ABSTRACT

A new and distinct cultivar of the Spray Class is provided that abundantly forms in clusters attractive double irregularly striped pale pink and cream blossoms. The blossoms possess no fragrance. An erect growth habit is exhibited. The foliage is semi-glossy and dark green and contrasts well with the striped blossoms. The disease resistance is very good. The plant is well suited for the production of cut floral sprays under greenhouse growing conditions.

1 Drawing Sheet

Botanical/commercial classification: *Rosa hybrida*/Spray Rose.
Varietal denomination: cv. 'JACrewhi'.

SUMMARY OF THE INVENTION

The present invention is a new and distinct cultivar of Spray Rose plant, botanically known as *Rosa hybrida,* and hereafter is referred to by the cultivar name 'JACrewhi'.

The new cultivar was created at Somis, Calif., U.S.A., by artificial pollination wherein two parents were crossed which previously had been studied in the hope that they would contribute the desired characteristics. The female parent (i.e., the seed parent) of the new cultivar was the 'JACeve' cultivar (non-patented in the United States) and the male parent (i.e., the pollen parent) was the 'JAComail' cultivar (non-patented in the United States). The parentage of the new cultivar can be summarized as follows:

'JACeve'×'JAComail'.

The seeds resulting from the above pollination were sown and small plants were obtained which were physically and biologically different from each other. Selective study resulted in the identification of a single plant of the new variety.

It was found that the Spray Rose plant of the present invention possesses the following combination of characteristics:

(a) an erect growth habit,
(b) forms in clusters attractive double irregularly striped pale pink and cream blossoms that possess no fragrance,
(c) forms sturdy stems,
(d) forms attractive dark green leaves having a semi-glossy aspect, and
(e) exhibits very good disease resistance.

The striped pale pink and cream inflorescence coloration contrasts nicely with the dark green foliage.

The new cultivar of the present invention can be readily distinguished from its ancestors. More specifically, the 'JACeve' female parent forms light pink flowers, and the 'JAComail' male parent forms pink and white striped flowers.

The new cultivar well meets the needs of the horticultural industry. It is particularly well-suited for use in the production of cut floral sprays under greenhouse growing conditions.

The new cultivar has been found to undergo asexual propagation at Somis, Calif., U.S.A., by budding and by the rooting of cuttings. Asexual propagation by these routes has shown that the characteristics of the new cultivar are firmly fixed and are strictly transmissible from one generation to another.

BRIEF DESCRIPTION OF THE PHOTOGRAPH

The accompanying photograph shows as nearly true as is reasonably possible to make the same in a color illustration of this character, typical mature plant specimens of the new cultivar. The attractive double striped pale pink and cream blossoms, dark green foliage, and stems are illustrated while present in a transparent vase. The plants were grown under standard greenhouse growing conditions.

DETAILED DESCRIPTION

The description is based upon the observation of plants of the new cultivar growing in a greenhouse at Somis, Calif., U.S.A. Colors are identified by reference to The R.H.S. Colour Chart of The Royal Horticultural Society, London. The growing conditions approximate those commonly utilized for the commercial production of cut roses.

Growth habit: Erect.

Foliage: Attractive dark green and semi-glossy on the upper surface. The leaf serration is simple and regular. The leaves consist of 3, 5 (most often) and 7 leaflets. The leaflets commonly average approximately 7 cm in length and approximately 5 cm in width at the widest point. The overall leaflet shape is ovate, the leaflet base is rounded, and the leaflet apex is cuspidate. The leaflets are relatively thick. The petioles possess a glandular surface texture, commonly are approximately 2 cm in length (from the branch to the first pair of leaflets), commonly are approximately 0.15 to 0.2 cm in diameter, are near Green Group 137A and 137B on the upper surface, and are near Yellow-Green Group 146B and 146C on the under surface. The stipules possess a smooth surface texture, commonly are approximately 1.8 cm in length on average, commonly are approximately 0.8 cm in width on average, are near Green Group 137B on the upper surface, and are near Green Group 138B on the under surface.

Stems: Sturdy and commonly possess rather large thorns (as illustrated). The thorns commonly measure approximately 0.8 cm in length on average, possess a narrow ovate base, are substantially straight on the upper surface, are concave on the under surface, and commonly are near Yellow-Green Group 144B in coloration.

Inflorescence: The blossoms are double and commonly are borne in sprays. The blossom coloration is attractive irregularly striped pale pink and cream. During the course of opening the upper petal surfaces commonly are near Red-Purple Group 60B and 60C with streaks of White Group 155B powdered with Red-Purple Group 60B and 60C, and the under petal surfaces commonly are near Red-Purple Group 60C and 60D with streaks of White Group 155B powdered with Red-Purple Group 60C and 60D. When fully open the upper petal surfaces commonly are near Red-Purple Group 61B and 61C suffused with Red Group 53B and 53C, and the under petal surfaces commonly are near Red-Purple Group 60C and 60D. Some dark purple-red coloration sometimes appears at the petal borders. Such appearance is influenced by the stage of the growing season. The blossoms possess no fragrance. The petals commonly number approximately 70 on average per flower, possess a relatively firm texture, and possess a wedge-shaped base and a cuspidate apex. The petals commonly measure approximately 3.5 cm in length on average and approximately 3 cm in width on average. No petaloids have been encountered during observations to date. The diameter of a fully open flower commonly is approximately 6 cm on average. The stamens commonly number approximately 30 on average and the pistils commonly number approximately 40 on average. The anthers commonly measure approximately 0.2 cm on average and are near Yellow-Orange Group 20A in coloration. The filaments commonly measure approximately 0.6 cm on average and are near Yellow Group 8D in coloration. The styles commonly are approximately 0.8 cm in length. The stigmas commonly are approximately 0.1 cm in size on average and near Yellow Group 8B in coloration. The receptacles commonly are approximately 0.4 cm in length on average, and approximately 0.8 cm in width on average. The sepals are five in number, approximately 2.5 cm in length on average, approximately 0.8 cm in width at the widest area, possess a narrow-pointed apex, and possess a tomentose upper surface and a smooth under surface. The pollen possesses a medium orange coloration. No hips have been observed during greenhouse growing conditions. The blossoms are long-lasting and commonly last approximately 18 to 20 days on the plant when grown under standard greenhouse growing conditions.

Disease resistance: Very good.

Propagation: Budding and the rooting of cuttings.

Usage: Production of cut floral sprays under greenhouse growing conditions. The petals commonly drop off cleanly before drying. The blossoms commonly last approximately 15 days on average when cut and placed in a vase.

I claim:

1. A new and distinct cultivar of *Rosa hybrida* plant having the following combination of characteristics:

(a) an erect growth habit, (b) forms in clusters attractive double irregularly striped pale pink and cream blossoms that possess no fragrance, (c) forms sturdy stems, (d) forms attractive dark green leaves having a semi-glossy aspect, and (e) exhibits very good disease resistance;

substantially as illustrated and described.

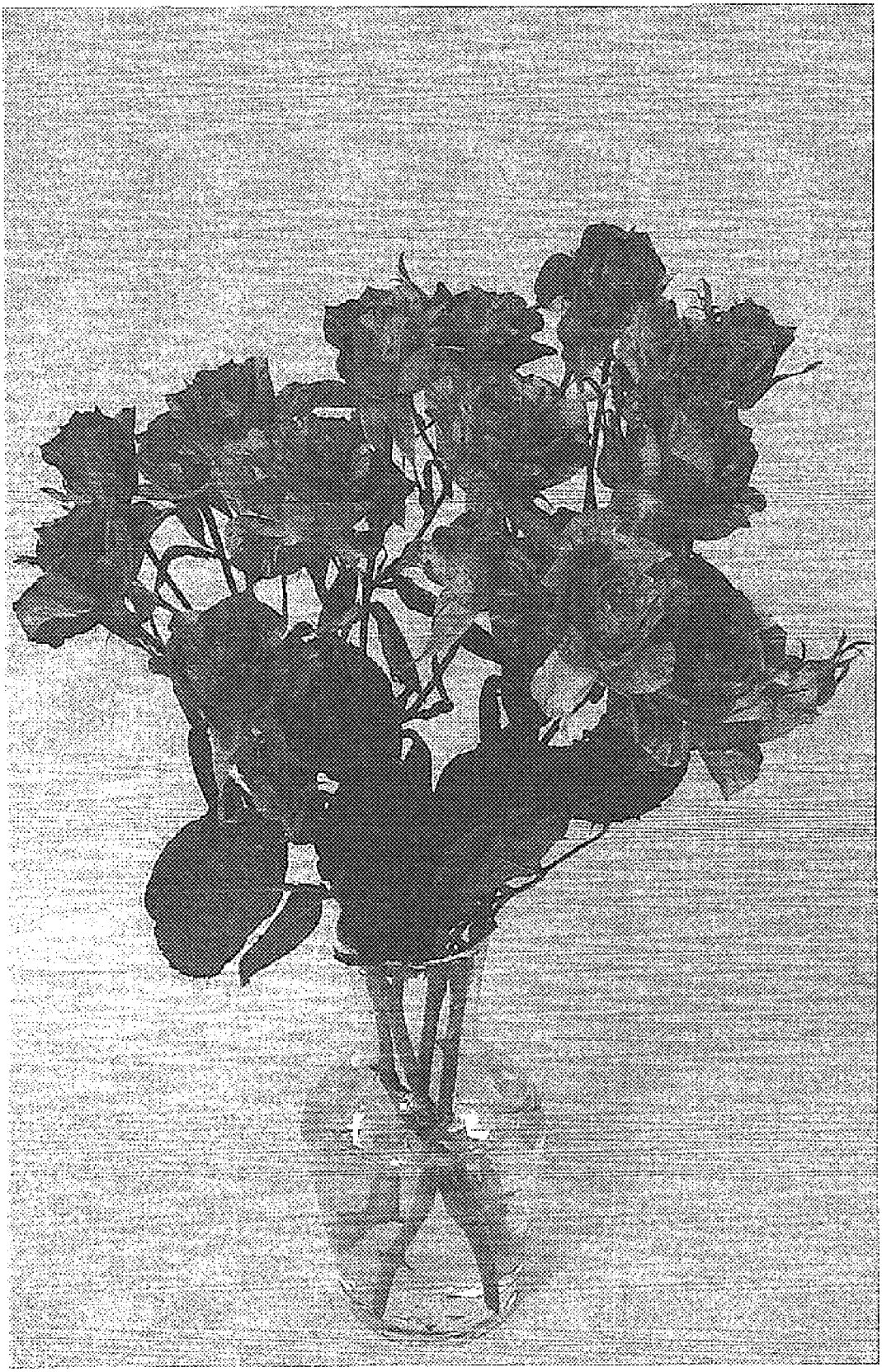

* * * * *